US011833291B2

(12) United States Patent
Patton et al.

(10) Patent No.: US 11,833,291 B2
(45) Date of Patent: *Dec. 5, 2023

(54) PRESERVATIVE-FREE SINGLE DOSE INHALER SYSTEMS

(71) Applicant: Aerami Therapeutics, Inc., Durham, NC (US)

(72) Inventors: John S. Patton, San Francisco, CA (US); Ryan S. Patton, San Francisco, CA (US); Mei-chang Kuo, Palo Alto, CA (US); Yehuda Ivri, Newport Beach, CA (US)

(73) Assignee: Aerami Therapeutics, Inc., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/874,531

(22) Filed: Jul. 27, 2022

(65) Prior Publication Data

US 2023/0051645 A1 Feb. 16, 2023

Related U.S. Application Data

(63) Continuation of application No. 16/685,382, filed on Nov. 15, 2019, now Pat. No. 11,400,241, which is a (Continued)

(51) Int. Cl.
*A61M 15/00* (2006.01)
*A61M 11/00* (2006.01)
(Continued)

(52) U.S. Cl.
CPC ....... *A61M 15/0028* (2013.01); *A61K 9/0073* (2013.01); *A61K 9/122* (2013.01);
(Continued)

(58) Field of Classification Search
CPC .......... A61M 15/0085; A61M 15/0091; A61M 15/08
See application file for complete search history.

(56) References Cited

U.S. PATENT DOCUMENTS 1,947,310 A 2/1934 Sample et al.
2,463,922 A 3/1949 Turner
(Continued)

FOREIGN PATENT DOCUMENTS

AU 2011205443 B2 1/2016
BR 112012017177-1 B1 7/2018
(Continued)

OTHER PUBLICATIONS

"On", Oxfordictionaries.com, Oxford Dictionaries, Jun. 21, 2016, 1 page.
(Continued)

*Primary Examiner* — Rachel T Sippel
(74) *Attorney, Agent, or Firm* — Kilpatrick Townsend & Stockton LLP

(57) ABSTRACT

An aerosolization system includes a container that is configured to deliver a unit dosage of a liquid when squeezed a single time. The system also includes an aerosolizer that is constructed of a housing defining a mouthpiece, and an aerosol generator disposed in the housing. The aerosol generator includes a vibratable membrane having a front face and a rear face, and a vibratable element used to vibrate the membrane. Further, the housing includes an opening that is adapted to receive a unit dosage of the liquid from the container. The opening provides a liquid path to the rear face of the vibratable membrane.

18 Claims, 8 Drawing Sheets

Related U.S. Application Data continuation of application No. 15/165,662, filed on May 26, 2016, now Pat. No. 10,525,214, which is a continuation of application No. 14/606,623, filed on Jan. 27, 2015, now Pat. No. 9,545,488, which is a continuation of application No. 14/039,254, filed on Sep. 27, 2013, now Pat. No. 9,004,061, which is a continuation of application No. 13/004,662, filed on Jan. 11, 2011, now Pat. No. 8,950,394.

(60) Provisional application No. 61/335,769, filed on Jan. 12, 2010.

(51) Int. Cl.
*A61K 9/00* (2006.01)
*A61K 38/28* (2006.01)
*A61K 9/12* (2006.01)
*A61K 33/30* (2006.01)
*A61M 16/00* (2006.01)

(52) U.S. Cl.
CPC .............. *A61K 33/30* (2013.01); *A61K 38/28* (2013.01); *A61M 11/00* (2013.01); *A61M 11/001* (2014.02); *A61M 11/005* (2013.01); *A61M 15/009* (2013.01); *A61M 15/0021* (2014.02); *A61M 15/0065* (2013.01); *A61M 15/0085* (2013.01); *A61M 15/0091* (2013.01); *A61M 2016/0021* (2013.01); *A61M 2016/0039* (2013.01); *A61M 2202/0468* (2013.01); *A61M 2205/3334* (2013.01); *A61M 2205/583* (2013.01); *A61M 2205/587* (2013.01)

(56) References Cited

U.S. PATENT DOCUMENTS

| | | |
|---|---|---|
| 3,789,843 A | 2/1974 | Armstrong et al. |
| 3,874,380 A | 4/1975 | Baum |
| 4,564,129 A | 1/1986 | Urban et al. |
| 4,694,977 A | 9/1987 | Graf et al. |
| 5,060,642 A | 10/1991 | Gilman |
| 5,164,740 A | 11/1992 | Ivri |
| 5,261,601 A | 11/1993 | Ross et al. |
| 5,333,106 A | 7/1994 | Lanpher et al. |
| 5,347,998 A | 9/1994 | Hodson et al. |
| 5,363,842 A | 11/1994 | Mishelevich et al. |
| 5,364,838 A | 11/1994 | Rubsamen |
| 5,385,180 A | 1/1995 | Wittman et al. |
| 5,479,920 A | 1/1996 | Piper et al. |
| 5,487,378 A | 1/1996 | Robertson et al. |
| 5,515,842 A | 5/1996 | Ramseyer et al. |
| 5,586,550 A | 12/1996 | Ivri et al. |
| 5,672,581 A | 9/1997 | Rubsamen et al. |
| 5,694,919 A | 12/1997 | Rubsamen et al. |
| 5,743,250 A | 4/1998 | Gonda et al. |
| 5,758,637 A | 6/1998 | Ivri et al. |
| 5,809,997 A | 9/1998 | Wolf |
| 5,884,620 A | 3/1999 | Gonda et al. |
| 5,915,378 A | 6/1999 | Lloyd et al. |
| 5,938,117 A | 8/1999 | Ivri |
| 5,941,240 A | 8/1999 | Gonda et al. |
| 6,014,970 A | 1/2000 | Ivri et al. |
| 6,062,212 A | 5/2000 | Davison et al. |
| 6,085,740 A | 7/2000 | Ivri et al. |
| 6,085,753 A | 7/2000 | Gonda et al. |
| 6,098,615 A | 8/2000 | Lloyd et al. |
| 6,131,567 A | 10/2000 | Gonda et al. |
| 6,164,498 A | 12/2000 | Faughey et al. |
| 6,205,999 B1 | 3/2001 | Ivri et al. |
| 6,257,454 B1 | 7/2001 | Ritsche |
| 6,312,665 B1 | 11/2001 | Modi |
| 6,408,854 B1 | 6/2002 | Gonda et al. |
| 6,427,682 B1 | 8/2002 | Klimowicz et al. |
| 6,467,476 B1 | 10/2002 | Ivri et al. |
| 6,540,153 B1 | 4/2003 | Ivri |
| 6,540,154 B1 | 4/2003 | Ivri et al. |
| 6,629,646 B1 | 10/2003 | Ivri |
| 6,640,804 B2 | 11/2003 | Ivri et al. |
| 6,647,987 B2 | 11/2003 | Gonda et al. |
| 6,688,304 B2 | 2/2004 | Gonda et al. |
| 6,712,762 B1 | 3/2004 | Lichter et al. |
| 6,729,327 B2 | 5/2004 | McFarland, Jr. |
| 6,748,946 B1 | 6/2004 | Rand et al. |
| 6,755,189 B2 | 6/2004 | Ivri et al. |
| 6,790,178 B1 | 9/2004 | Mault et al. |
| 6,814,071 B2 | 11/2004 | Klimowicz et al. |
| 6,921,020 B2 | 7/2005 | Ivri |
| 6,926,208 B2 | 8/2005 | Ivri |
| 6,958,691 B1 | 10/2005 | Anderson et al. |
| 6,978,941 B2 | 12/2005 | Litherland et al. |
| 7,028,686 B2 | 4/2006 | Gonda et al. |
| 7,032,590 B2 | 4/2006 | Loeffler et al. |
| 7,040,549 B2 | 5/2006 | Ivri et al. |
| 7,066,398 B2 | 6/2006 | Borland et al. |
| 7,083,112 B2 | 8/2006 | Ivri |
| 7,100,600 B2 | 9/2006 | Loeffler et al. |
| 7,108,197 B2 | 9/2006 | Ivri |
| 7,117,867 B2 | 10/2006 | Cox et al. |
| 7,174,888 B2 | 2/2007 | Ivri et al. |
| 7,195,011 B2 | 3/2007 | Loeffler et al. |
| 7,219,664 B2 | 5/2007 | Ruckdeschel et al. |
| 7,448,375 B2 | 11/2008 | Gonda et al. |
| 7,451,760 B2 | 11/2008 | Denyer et al. |
| 7,600,511 B2 | 10/2009 | Power et al. |
| 7,600,512 B2 | 10/2009 | Lee et al. |
| 7,628,339 B2 | 12/2009 | Ivri et al. |
| 7,683,029 B2 | 3/2010 | Hindle et al. |
| 7,819,115 B2 | 10/2010 | Sexton et al. |
| 7,886,783 B2 | 2/2011 | Rindy et al. |
| 8,082,918 B2 | 12/2011 | Jansen et al. |
| 8,326,964 B1 | 12/2012 | Chourey et al. |
| 8,736,227 B2 | 5/2014 | Chadbourne et al. |
| 8,950,394 B2 | 2/2015 | Patton et al. |
| 9,004,061 B2 | 4/2015 | Patton et al. |
| 9,180,261 B2 | 11/2015 | Patton et al. |
| 9,545,488 B2 | 1/2017 | Patton et al. |
| 10,525,214 B2 | 1/2020 | Patton et al. |
| 11,400,241 B2 | 8/2022 | Patton et al. |
| 2001/0037805 A1 | 11/2001 | Gonda et al. |
| 2001/0039948 A1 | 11/2001 | Sexton et al. |
| 2002/0129813 A1 | 9/2002 | Litherland et al. |
| 2003/0019493 A1 | 1/2003 | Narayan et al. |
| 2003/0041859 A1 | 3/2003 | Abrams et al. |
| 2003/0072740 A1 | 4/2003 | Milstein et al. |
| 2003/0101991 A1 | 6/2003 | Trueba |
| 2003/0150445 A1 | 8/2003 | Power et al. |
| 2003/0150446 A1 | 8/2003 | Patel et al. |
| 2004/0100509 A1 | 5/2004 | Sommerer et al. |
| 2004/0134494 A1 | 7/2004 | Papania et al. |
| 2004/0154617 A1 | 8/2004 | Enk |
| 2004/0223917 A1 | 11/2004 | Hindle et al. |
| 2004/0256488 A1 | 12/2004 | Loeffler et al. |
| 2005/0011514 A1 | 1/2005 | Power et al. |
| 2005/0030953 A1 | 2/2005 | Vasudevan et al. |
| 2005/0133024 A1 | 6/2005 | Coifman |
| 2005/0166913 A1 | 8/2005 | Sexton et al. |
| 2005/0172958 A1 | 8/2005 | Singer et al. |
| 2005/0240084 A1 | 10/2005 | Morice et al. |
| 2006/0239930 A1 | 10/2006 | Lamche et al. |
| 2006/0261084 A1 | 11/2006 | Grey et al. |
| 2007/0074722 A1 | 4/2007 | Giroux et al. |
| 2007/0113841 A1 | 5/2007 | Fuchs |
| 2007/0163572 A1 | 7/2007 | Addington et al. |
| 2007/0209659 A1 | 9/2007 | Ivri et al. |
| 2008/0017188 A1 | 1/2008 | Pardonge et al. |
| 2008/0020794 A1 | 1/2008 | Garon et al. |
| 2008/0029083 A1 | 2/2008 | Masada et al. |
| 2008/0060641 A1 | 3/2008 | Smith et al. |
| 2008/0148193 A1 | 6/2008 | Moetteli |
| 2008/0184993 A1 | 8/2008 | Patel et al. |
| 2008/0220747 A1 | 9/2008 | Ashkenazi et al. |
| 2008/0233053 A1 | 9/2008 | Gross et al. |

(56) References Cited

U.S. PATENT DOCUMENTS

| | | |
|---|---|---|
| 2008/0306794 A1 | 12/2008 | Cohen et al. |
| 2009/0025718 A1 | 1/2009 | Denyer et al. |
| 2009/0095292 A1 | 4/2009 | Hamano et al. |
| 2009/0099065 A1 | 4/2009 | Madsen et al. |
| 2009/0140010 A1 | 6/2009 | Pruvot |
| 2009/0151718 A1 | 6/2009 | Hunter et al. |
| 2009/0156952 A1 | 6/2009 | Hunter et al. |
| 2009/0157037 A1 | 6/2009 | Iyer et al. |
| 2009/0194104 A1 | 8/2009 | Van Sickle |
| 2009/0241948 A1 | 10/2009 | Clancy et al. |
| 2009/0301472 A1 | 12/2009 | Kim et al. |
| 2010/0075001 A1 | 3/2010 | Succar et al. |
| 2010/0094099 A1 | 4/2010 | Levy et al. |
| 2010/0153544 A1 | 6/2010 | Krassner et al. |
| 2010/0154793 A1 | 6/2010 | Kobayashi et al. |
| 2010/0180890 A1 | 7/2010 | Nobutani |
| 2010/0236545 A1 | 9/2010 | Kern |
| 2010/0250280 A1 | 9/2010 | Sutherland |
| 2010/0250697 A1 | 9/2010 | Hansen et al. |
| 2010/0319686 A1 | 12/2010 | Schennum |
| 2010/0326436 A1 | 12/2010 | Kaneko |
| 2011/0022350 A1 | 1/2011 | Chatterjee |
| 2011/0114089 A1 | 5/2011 | Andersen et al. |
| 2011/0125594 A1 | 5/2011 | Brown et al. |
| 2011/0168170 A1 | 7/2011 | Patton et al. |
| 2011/0168172 A1 | 7/2011 | Patton et al. |
| 2011/0225008 A1 | 9/2011 | Elkouh et al. |
| 2011/0246440 A1 | 10/2011 | Kocks et al. |
| 2011/0253139 A1 | 10/2011 | Guthrie et al. |
| 2012/0032901 A1 | 2/2012 | Kwon |
| 2012/0037154 A1 | 2/2012 | Gallem et al. |
| 2012/0069803 A1 | 3/2012 | Iwamura et al. |
| 2012/0116241 A1 | 5/2012 | Shieh et al. |
| 2012/0144303 A1 | 6/2012 | Cricks et al. |
| 2012/0155987 A1 | 6/2012 | Watanabe |
| 2012/0285236 A1 | 11/2012 | Haartsen et al. |
| 2013/0155987 A1 | 6/2013 | Lan et al. |
| 2013/0269684 A1 | 10/2013 | Patton |
| 2013/0269694 A1 | 10/2013 | Patton et al. |
| 2013/0318471 A1 | 11/2013 | Freyhult et al. |
| 2014/0010187 A1 | 1/2014 | Huang et al. |
| 2014/0041653 A1 | 2/2014 | Patton et al. |
| 2014/0362831 A1 | 12/2014 | Young |
| 2015/0092590 A1 | 4/2015 | Zhu et al. |
| 2015/0196721 A1 | 7/2015 | Patton et al. |
| 2016/0271346 A1 | 9/2016 | Patton et al. |
| 2019/0015611 A1 | 1/2019 | Patton et al. |

FOREIGN PATENT DOCUMENTS

| | | |
|---|---|---|
| BR | 112014025878-3 B1 | 4/2022 |
| CA | 2786128 C | 4/2018 |
| CN | 1062091 A | 6/1992 |
| CN | 2406684 Y | 11/2000 |
| CN | 1303309 A | 7/2001 |
| CN | 2461580 Y | 11/2001 |
| CN | 101080249 A | 11/2007 |
| CN | 101300041 A | 11/2008 |
| CN | 101316660 A | 12/2008 |
| CN | 101495168 A | 7/2009 |
| CN | 102740911 A | 10/2012 |
| CN | 102740915 A | 10/2012 |
| CN | 104470567 A | 3/2015 |
| CN | 104470568 A | 3/2015 |
| CN | 102740915 B | 1/2016 |
| CN | 104470567 B | 11/2018 |
| EP | 0111875 A1 | 6/1984 |
| EP | 0311863 A2 | 4/1989 |
| EP | 2523712 A1 | 11/2012 |
| EP | 2523716 A1 | 11/2012 |
| EP | 2838593 A1 | 2/2015 |
| EP | 2838592 B1 | 5/2018 |
| FR | 2835435 A1 | 8/2003 |
| HK | 1174579 | 6/2004 |
| HK | 1174580 | 6/2013 |
| JP | 08502689 A | 3/1996 |
| KR | 1020120115389 A | 10/2012 |
| KR | 20120125494 A | 11/2012 |
| MX | 340395 B | 7/2016 |
| RU | 2188041 C2 | 8/2002 |
| RU | 2336906 C2 | 10/2008 |
| RU | 2460677 C2 | 9/2012 |
| RU | 2012134402 A | 2/2014 |
| RU | 2012134422 A | 2/2014 |
| RU | 2548755 | 4/2015 |
| RU | 2559171 C2 | 8/2015 |
| RU | 2637285 C2 | 12/2017 |
| WO | 9822290 A1 | 5/1998 |
| WO | 03030829 A2 | 4/2003 |
| WO | 2004028608 A1 | 4/2004 |
| WO | 2005065756 A2 | 7/2005 |
| WO | 2006006963 A3 | 6/2006 |
| WO | 2006062449 A1 | 6/2006 |
| WO | 2007047948 A2 | 4/2007 |
| WO | 2008121610 A1 | 10/2008 |
| WO | 2009111612 A1 | 9/2009 |
| WO | 2010002421 A1 | 1/2010 |
| WO | 2010066714 A1 | 6/2010 |
| WO | 2010141803 A2 | 12/2010 |
| WO | 2011088070 A1 | 7/2011 |
| WO | 2011130183 A2 | 10/2011 |
| WO | 2013158352 A1 | 10/2013 |
| WO | 2013158353 A1 | 10/2013 |

OTHER PUBLICATIONS

U.S. Appl. No. 13/004,645 , Final Office Action, dated Sep. 20, 2013, 17 pages.
U.S. Appl. No. 13/004,645 , Final Office Action, dated Apr. 29, 2014, 21 pages.
U.S. Appl. No. 13/004,645 , Final Office Action, dated Mar. 10, 2015, 24 pages.
U.S. Appl. No. 13/004,645 , Non-Final Office Action, dated Mar. 13, 2013, 15 pages.
U.S. Appl. No. 13/004,645 , Non-Final Office Action, dated Nov. 25, 2013, 19 pages.
U.S. Appl. No. 13/004,645 , Notice of Allowance, dated Jul. 8, 2015, 11 pages.
U.S. Appl. No. 13/004,662 , Advisory Action, dated Sep. 6, 2013, 3 pages.
U.S. Appl. No. 13/004,662 , Final Office Action, dated Aug. 22, 2014, 16 pages.
U.S. Appl. No. 13/004,662 , Final Office Action, dated Jul. 18, 2013, 17 pages.
U.S. Appl. No. 13/004,662 , Non-Final Office Action, dated Jan. 22, 2013, 10 Pages.
U.S. Appl. No. 13/004,662 , Non-Final Office Action, dated Apr. 18, 2014, 15 pages.
U.S. Appl. No. 13/004,662 , Non-Final Office Action, dated Oct. 10, 2013, 15 pages.
U.S. Appl. No. 13/004,662 , Notice of Allowance, dated Nov. 24, 2014, 13 pages.
U.S. Appl. No. 13/830,511 , Advisory Action, dated Apr. 5, 2018, 5 pages.
U.S. Appl. No. 13/830,511 , Advisory Action, dated Feb. 1, 2016, 7 pages.
U.S. Appl. No. 13/830,511 , Final Office Action, dated Jul. 26, 2016, 26 pages.
U.S. Appl. No. 13/830,511 , Final Office Action, dated Jan. 8, 2018, 38 pages.
U.S. Appl. No. 13/830,511 , Final Office Action, dated Oct. 30, 2015, 45 pages.
U.S. Appl. No. 13/830,511 , Non-Final Office Action, dated May 15, 2018, 26 pages.
U.S. Appl. No. 13/830,511 , Non-Final Office Action, dated Apr. 5, 2017, 29 pages.
U.S. Appl. No. 13/830,511 , Non-Final Office Action, dated Jun. 4, 2015, 36 pages.

(56) References Cited

OTHER PUBLICATIONS

U.S. Appl. No. 13/830,511, Non-Final Office Action, dated Mar. 11, 2016, 45 pages.
U.S. Appl. No. 13/830,551, Final Office Action, dated Jul. 31, 2015, 15 pages.
U.S. Appl. No. 13/830,551, Final Office Action, dated Sep. 22, 2016, 17 pages.
U.S. Appl. No. 13/830,551, Final Office Action, dated Sep. 10, 2018, 18 pages.
U.S. Appl. No. 13/830,551, Final Office Action, dated Oct. 3, 2017, 20 pages.
U.S. Appl. No. 13/830,551, Non-Final Office Action, dated Feb. 27, 2015, 13 pages.
U.S. Appl. No. 13/830,551, Non-Final Office Action, dated Apr. 11, 2016, 14 pages.
U.S. Appl. No. 13/830,551, Non-Final Office Action, dated May 26, 2017, 18 pages.
U.S. Appl. No. 13/830,551, Non-Final Office Action, dated Feb. 9, 2018, 23 pages.
U.S. Appl. No. 13/840,588, Final Office Action, dated Sep. 11, 2015, 30 pages.
U.S. Appl. No. 13/840,588, Final Office Action, dated Jun. 30, 2016, 32 pages.
U.S. Appl. No. 13/840,588, Non-Final Office Action, dated Feb. 24, 2016, 15 pages.
U.S. Appl. No. 13/840,588, Non-Final Office Action, dated Feb. 9, 2017, 25 pages.
U.S. Appl. No. 13/840,588, Non-Final Office Action, dated Mar. 16, 2015, 27 pages.
U.S. Appl. No. 14/039,254, Advisory Action, dated Sep. 10, 2014, 3 pages.
U.S. Appl. No. 14/039,254, "Corrected Notice of Allowability", dated Mar. 18, 2015, 6 pages.
U.S. Appl. No. 14/039,254, Final Office Action, dated Jun. 11, 2014, 19 pages.
U.S. Appl. No. 14/039,254, Non-Final Office Action, dated Feb. 10, 2014, 17 pages.
U.S. Appl. No. 14/039,254, Notice of Allowance, dated Dec. 24, 2014, 14 pages.
U.S. Appl. No. 14/606,623, Non-Final Office Action, dated Mar. 8, 2016, 7 pages.
U.S. Appl. No. 14/606,623, "Notice of Allowability", dated Dec. 14, 2016, 4 pages.
U.S. Appl. No. 14/606,623, Notice of Allowance, dated Apr. 18, 2016, 8 pages.
U.S. Appl. No. 15/165,662, Advisory Action, dated Jul. 10, 2017, 3 pages.
U.S. Appl. No. 15/165,662, Advisory Action, dated Jul. 24, 2018, 3 pages.
U.S. Appl. No. 15/165,662, Advisory Action, dated Jul. 29, 2019, 3 pages.
U.S. Appl. No. 15/165,662, Final Office Action, dated Jan. 30, 2017, 17 pages.
U.S. Appl. No. 15/165,662, Final Office Action, dated May 7, 2018, 19 pages.
U.S. Appl. No. 15/165,662, Final Office Action, dated May 10, 2019, 20 pages.
U.S. Appl. No. 15/165,662, Non-Final Office Action, dated Aug. 30, 2017, 17 pages.
U.S. Appl. No. 15/165,662, Non-Final Office Action, dated Aug. 8, 2016, 17 pages.
U.S. Appl. No. 15/165,662, Non-Final Office Action, dated Sep. 6, 2018, 19 pages.
U.S. Appl. No. 15/165,662, Notice of Allowance, dated Sep. 3, 2019, 8 pages.
U.S. Appl. No. 16/133,484, Advisory Action, dated Mar. 26, 2021, 4 pages.
U.S. Appl. No. 16/133,484, Advisory Action, dated Jun. 8, 2022, 5 pages.
U.S. Appl. No. 16/133,484, Final Office Action, dated Jan. 22, 2021, 26 pages.
U.S. Appl. No. 16/133,484, Final Office Action, dated Feb. 22, 2022, 30 pages.
U.S. Appl. No. 16/133,484, Non-Final Office Action, dated Jul. 17, 2020, 19 pages.
U.S. Appl. No. 16/133,484, Non-Final Office Action, dated Nov. 9, 2021, 31 pages.
U.S. Appl. No. 16/133,484, Non-Final Office Action, dated Oct. 21, 2022, 35 pages.
U.S. Appl. No. 16/685,382, Notice of Allowance, dated Mar. 29, 2022, 9 pages.
Application No. AU2011205443, "First Examination Report", dated Mar. 13, 2015, 3 pages.
Application no. AU2011205443, "Notice of Acceptance", dated Sep. 14, 2015, 3 pages.
Application No. BR112012017177-1, Notice of Allowance, dated Jul. 28, 2020, 1 page, no English translation available.
Application No. BR112012017177-1, Office Action, dated Feb. 27, 2020, 3 pages, no English translation available.
Application No. BR112014025878-3, Office Action, dated Oct. 13, 2021, 5 pages, no English translation available.
Application No. BR112014025878-3, Notice of Allowance, dated Feb. 8, 2022, no English translation available.
Application No. BR112014025878-3, Office Action, dated Jan. 14, 2020, 7 pages (pp. 1-3 English translation, pp. 4-7 original document).
Application No. CA 2,786,128, Notice of Allowance, dated Sep. 5, 2017, 1 page.
Application No. CA 2,786,128, Office Action, dated Nov. 23, 2016, 3 pages.
Application No. CA 2,786,131, Office Action, dated Nov. 8, 2016, 4 pages.
Application No. CN201180005836.5, Office Action, dated Nov. 1, 2013, 9 pages (pp. 1-4 English, pp. 5-9 original document).
Application No. CN201180005839.9, Notice of Decision to Grant, dated Sep. 18, 2015, 4 pages.
Application No. CN201180005839.9, Office Action, dated Jun. 17, 2014, 12 pages, (pp. 1-3 English, pp. 4-12 original document).
Application No. CN201180005839.9, Office Action, dated Mar. 3, 2015, 12 pages (pp. 1-7 English, pp. 8-12 original document).
Application No. CN201380031665.2, Notice of Decision to Grant, dated Aug. 17, 2018, 6 pages.
Application No. CN201380031665.2, Office Action, dated Mar. 25, 2016, 20 pages (pp. 1-10 English, pp. 11-20 original document).
Application No. CN201380031665.2, Office Action, dated Mar. 27, 2018, 11 pages, no English translation available.
Application No. CN201380031665.2, Office Action, dated Sep. 11, 2017, 11 pages, no English translation available.
Application No. CN201380031665.2, Office Action, dated Jan. 11, 2017, 17 pages, pp. 1-10 English, pp. 11-17 original document.
Application No. CN201380031812.6, Office Action, dated Jan. 24, 2017, 11 pages (pp. 1-7 English, pp. 8-11 original document).
Application No. CN201380031812.6, Office Action, dated Apr. 19, 2016, 12 pages (pp. 1-6 English, pp. 7-12 original document).
Application No. EP11733286.6, Extended European Search Report, dated Aug. 4, 2015, 5 pages.
Application No. EP11733286.6, Notice of Decision to Grant, dated Oct. 15, 2020, 1 page.
Application No. EP11733286.6, Office Action, dated Mar. 20, 2018, 4 pages.
Application No. EP11733287.4, Extended European Search Report, dated Jul. 12, 2013, 7 pages.
Application No. EP11733287.4, Office Action, dated Aug. 9, 2016, 5 pages.
Application No. EP13778058.1, Extended European Search Report, dated Oct. 7, 2015, 5 pages.
Application No. EP13778248.8, Extended European Search Report, dated Oct. 26, 2015, 12 pages.
Application No. EP13778248.8, Notice of Decision to Grant, dated May 4, 2018, 1 page.
Application No. EP13778248.8, Office Action, dated Mar. 24, 2017, 5 pages.

(56) References Cited

OTHER PUBLICATIONS

Application No. IN1921/MUMNP/2012, "First Examination Report", dated May 10, 2019, 7 pages.
Application No. KR10-2012-7021081, Office Action, dated Aug. 30, 2017, 8 pages (pp. 1-4 English, pp. 5-8 original document).
Application No. KR10-2012-7021081, Office Action, dated Nov. 15, 2016, 12 pages (pp. 1-6 English, pp. 7-12 original document).
Application No. KR10-2012-7021085, Office Action, dated Nov. 15, 2016, 10 pages (pp. 1-12 English, pp. 13-22 original document).
Liu et al., "Pulmonary Delivery of Free and Liposomal Insulin", Pharmaceutical Research, Kluwer Academic Publishers, vol. 10, No. 2, Feb. 1, 1993, pp. 228-232.
Application No. MX/A/2012/008010, Notice of Allowance, dated May 30, 2016, 2 pages, no English translation available.
Application No. MX/A/2012/008010, Office Action, dated Feb. 12, 2015, 2 pages, no English translation available.
Application No. MX/A/2012/008010, Office Action, dated Mar. 10, 2015, 2 pages, no English translation available.
Application No. MX/A/2012/008010, Office Action, dated Sep. 17, 2015, 3 pages, no English translation available.
Application No. MX/A/2012/008010, Office Action, dated Nov. 12, 2014, 5 pages, no English translation available.
Application No. MX/A/2012/008010, Office Action, dated Jul. 15, 2014, 6 pages, no English translation available.
Application No. MX/A/2012/008011, Notice of Allowance, dated Sep. 14, 2016, 1 page, no English translation available.
Application No. MX/A/2012/008011, Office Action, dated Apr. 7, 2016, 3 pages, no English translation available.
Application No. PCT/US2011/020925, International Preliminary Report on Patentability, dated Jul. 26, 2012, 6 pages.
Application No. PCT/US2011/020925, International Search Report and Written Opinion, dated Mar. 14, 2011, 7 pages.
Application No. PCT/US2011/020926, International Search Report and Written Opinion, dated Mar. 14, 2011, 11 pages.
Application No. PCT/US2013/034354, International Preliminary Report on Patentability, dated Oct. 30, 2014, 10 pages.
Application No. PCT/US2013/034354, International Search Report and Written Opinion, dated Jun. 25, 2013, 12 pages.
Application No. PCT/US2013/034359, International Preliminary Report on Patentability, dated Oct. 30, 2014, 7 pages.
Application No. PCT/US2013/034359, International Search Report and Written Opinion, dated Jun. 28, 2013, 9 pages.
Application No. RU2012134422, Notice of Decision to Grant, dated Feb. 17, 2015, 13 pages (pp. 1-6 English translation, pp. 7-13 original document).
Application No. RU2012134422, Office Action, dated Oct. 20, 2014, 5 pages (pp. 1-2 English, pp. 3-5 original document).
Application No. RU2014145835, Office Action, dated Feb. 6, 2017, 7 pages, no English translation available.
Application No. RU2014145836, Notice of Decision to Grant, dated Jul. 27, 2017, 8 pages, no English translation available.
Application No. RU2014145836, Office Action, dated Jan. 18, 2017, 5 pages, no English translation available.
Spector et al., "Compliance of Patients with Asthma with an Experimental Aerosolized Medication: Implications for Controlled Clinical Trials", Journal of Aliergy and Clinical Immunology, vol. 77, No. 1, Jan. 1, 1986, pp. 65-70.

PRESERVATIVE-FREE SINGLE DOSE INHALER SYSTEMS

CROSS-REFERENCES TO RELATED APPLICATIONS

This application is a continuation of U.S. patent application Ser. No. 16/685,382, filed Nov. 15, 2019, which is a continuation of U.S. patent application Ser. No. 15/165,662, filed on May 26, 2016, now U.S. Pat. No. 10,525,214, which is a continuation of U.S. patent application Ser. No. 14/606,623, filed on Jan. 27, 2015, now U.S. Pat. No. 9,545,488, which is a continuation of U.S. patent application Ser. No. 14/039,254, filed on Sep. 27, 2013, now U.S. Pat. No. 9,004,061, which is a continuation of U.S. patent application Ser. No. 13/004,662, filed on Jan. 11, 2011, now U.S. Pat. No. 8,950,394, which claims priority from U.S. Provisional Application No. 61/335,769, filed on Jan. 12, 2010, which are incorporated by reference herein in their entireties.

FIELD OF THE INVENTION

This invention relates generally to a single dose inhaler and insulin formation containers. The inhaler dispenses aerosolized pharmaceutical agents for local or systemic inhalation drug delivery to the lungs. The invention is particularly, but not exclusively, useful for delivery of preservative free doses of insulin for treating type I and/or type II diabetic patients.

BACKGROUND OF THE INVENTION

Various types of inhalers exist for aerosolizing liquids. For example, U.S. Pat. No. 5,586,550, incorporated herein by reference, describes an inhaler which comprises a dispensing apparatus in which a membrane with tapered apertures is vibrated such that liquid in contact with a rear face of the membrane is dispensed from a front face of the membrane as an aerosol.

While effective at nebulizing liquids, such inhalers may not be particularly suited for certain applications, such as aerosolizing unit doses of insulin for pulmonary delivery.

Hence, the invention provides inhalers for delivering doses in a repeatable and predictable fashion. As described hereinafter, the inhalers of the invention may find particular use in aerosolizing liquid insulin for pulmonary delivery.

BRIEF SUMMARY OF THE INVENTION

The invention provides various aerosolization systems, including containers for supplying liquid to inhalers, as well as methods for their use. In one exemplary embodiment, the invention provides an aerosolization system that comprises a squeezable container having a resilient container body. The container is configured to deliver a unit dosage of a liquid when squeezed a single time.

The system further includes an aerosolizer that comprises a housing defining a mouthpiece, and an aerosol generator disposed in the housing. The aerosol generator comprises a vibratable membrane having a front face and a rear face, and a vibratable element used to vibrate the membrane. Further, the housing includes an opening that is adapted to receive a unit dosage of the liquid from the container. The opening provides a liquid path to the rear face of the vibratable membrane.

In one aspect, the aerosolizer includes a hollow needle that is configured to pierce the squeezable container and to supply the liquid to the rear face of the vibratable membrane. Also, the squeezable container may comprise a blister containing a single unit dosage. For example, the blister may comprise a blow-fill-seal container that contains a preservative free solution. The blister may further comprise a squeezable body containing the solution, a twist off top and a tab adapted to display information about the solution.

In a further aspect, the single unit dosage has a concentration in the range from about 200 insulin units ("IU")/ml to about 800 IU/ml.

In another embodiment, the container comprises a bottle containing of volume of the liquid. In one aspect, the bottle may include a metering valve that permits dispensing of a discrete droplet of the liquid each time the bottle is squeezed. In other cases, the size of the droplet may be controlled based at least in part on the diameter of the tip of the bottle and the viscosity of the liquid.

The invention further provides another aerosolization system that comprises a container in the form of an ampoule containing a capillary that holds a single unit dosage of a liquid. The system also includes an aerosolizer comprising a housing defining a mouthpiece, and an aerosol generator disposed in the housing. The aerosol generator comprises a vibratable membrane having a front face and a rear face, and a vibratable element used to vibrate the membrane. Also, the housing includes an opening that is adapted to receive a unit dosage of the liquid from the container. Further, the opening provides a liquid path to the rear face of the vibratable membrane.

In one particular aspect, the ampoule further comprises a snap-off top and a snap-off bottom. The capillary is sized such that surface tension in the capillary prevents leakage of the liquid after removal of the top but prior to removal of the bottom.

A further embodiment of the invention provides an aerosolization system having a container comprising a container body that holds a supply of liquid, and a plunger device that is movable to dispense a single unit dosage of a liquid from the container upon operation of the plunger device a set distance. An aerosolizer comprises a housing defining a mouthpiece, and an aerosol generator disposed in the housing. The aerosol generator comprises a vibratable membrane having a front face and a rear face, and a vibratable element used to vibrate the membrane. Further, the housing includes an opening that is adapted to receive a unit dosage of the liquid from the container. The opening provides a liquid path to the rear face of the vibratable membrane.

In one aspect, the container further includes a metering device that is rotated to control movement of the plunger in order to set a single unit dosage amount.

BRIEF DESCRIPTION OF THE DRAWINGS

FIG. 1 is a perspective, partial cut-away view of one embodiment of a dispensing apparatus and squeezable container according to the invention.

FIG. 2 is a more detailed view of the dispensing apparatus and container of FIG. 1.

FIG. 3 is illustrates the dispensing device of FIG. 1, showing a more detailed view of a seat for holding the container and a needle for supplying dispensed liquid to an aerosol generator.

FIG. 4 is a perspective view of another embodiment of a dispensing apparatus and an a squeezable bottle according to the invention.

FIG. 4A is a cross sectional schematic view of a portion of the bottle of FIG. 4 in a closed position.

FIG. 4B is a cross sectional schematic view of a portion of the bottle of FIG. 4 in an open position FIG. 5 illustrates another embodiment of a container for dispensing a unit volume of a liquid according to the invention.

DETAILED DESCRIPTION OF THE INVENTION

Figure 1:
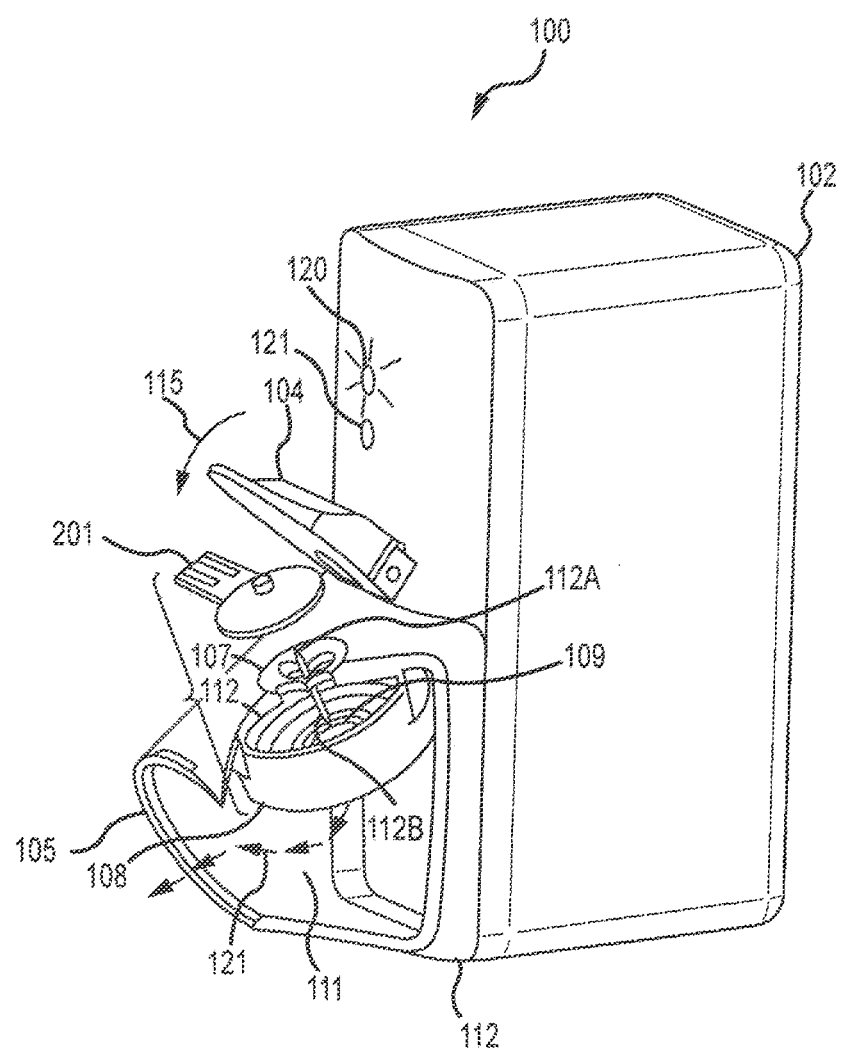

Certain aspects of the invention describe an aerosolizing apparatus comprising a housing defining a dispensing outlet, a vibratable membrane having a front face exposed at the outlet and a rear face for receiving a liquid to be dispensed, and a vibrating mechanism connected to the housing and operable to vibrate the membrane to dispense aerosol of the liquid through the membrane. A liquid delivery system is used to deliver a metered quantity of the liquid from to the rear face of the membrane. In this way, a metered quantity of liquid is dispensable at the outlet by operating the vibrating mechanism for an operating period sufficient to completely aerosolize the metered quantity of the rear face.

An advantage of such an apparatus is that it facilitates the dispensing of substantially all of the liquid coming into contact with the rear face of the membrane as a single dose, especially when the metered dose is relatively small in volume. By dispensing the entire dose, the membrane is essentially free of liquid from one dose to the next. In this way, it is thereby possible to avoid contact between liquid and ambient air during periods of non-use between successive uses. For pharmaceutical preparations this is particularly important since it may obviate the need for the use of preservatives in the liquid and avoids evaporative losses. For example, various preservative free insulin formulations that may be used include those described in copending U.S. application Ser. No. 13/004,662, entitled "Preservative Free Insulin Formulations and Systems and Methods for Aerosolizing" and filed on the same date as the present application, previously incorporated by reference.

The liquid supply system in one embodiment may comprise a deformable thin-wall blister which contains a pharmaceutical agent. The supply system further comprises a mechanical press configured to deform the thin-walled blister such that a single, preservative free unit dose is delivered. The press mechanism is provided with a dispensing station provided with a piercing needle operable to pierce the blister and release its content upon actuation.

In one aspect, the needle has two ends, with the first end protruding from the surface of the dispensing station and a second end extending to rear face of the aerosol generator. In use the blister is seated in the dispensing station and the press mechanism forces the blister toward the needle which pierces through the thin wall. In this way, the needle provides a conduit for moving the liquid from the blister to the rear face of the vibratable membrane. When the press mechanism is released the blister expands and returns to its natural position. This expansion creates a suction action which removes the liquid from the needle and prevents dry out and clogging.

In a further aspect, the blister has a bellows shaped geometry which can elastically expand and compress. The term elastically expand and compress includes when the blister is fully compressed the internal stresses are still within the elastic range of the material in use, thus, the blister can return to its natural position when the press mechanism is released. In one particular aspect, the pharmaceutical agent fills at least 80% the internal volume of the blister and more preferably more than 90% of the volume. This prevents movement of liquid which in some cases may cause aggregation of the composition.

Conveniently, the end of the needle may be positioned in close proximity to the rear face of the vibratable membrane. Further, the housing may define a duct communicating between an air inlet and an outlet port. The dispensing outlet is located in the duct intermediate the air inlet and the outlet port such that the front face of the membrane is exposed to air within the duct. The outlet port may be a mouthpiece for inhalation or an adapter for nasal use.

Such an arrangement is particularly useful in the administration of inhaled pharmaceutical liquid products where it is required that a fine aerosol of liquid be entrained in an inhaled air flow passing through the mouthpiece. One example of such a liquid is an insulin composition.

Referring now to FIG. 1, one embodiment of an inhaler will be described. FIG. 1 illustrates a partially cut-away view of the single-dose-inhaler 100 and a unit dose blister 201 package for supplying a metered quantity of insulin to the inhaler. Inhaler 100 comprises two subassemblies 102 and 112. The first subassembly 102 defines a compartment for the electronic circuitry and the batteries, and the second subassembly 112 defines a housing with a dispensing outlet 105 and contains a vibratable membrane aerosol generator 108 and a dispensing mechanism 104. Aerosol generator 108 has a front face exposed at the outlet duct 111 and a rear face 109 contacted in use by liquid to be dispensed. Aerosol generator 108 is connected to the housing of subassembly 112 and is operable to dispense the active pharmaceutical agent as an aerosol through the mouthpiece 105. Exemplary aerosol generators that may be used are also described in U.S. Pat. Nos. 5,164,740; 6,629,646; 6,926,208; 7,108,197; 5,938,117; 6,540,153; 6,540,154; 7,040,549; 6,921,020; 7,083,112; 7,628,339; 5,586,550; 5,758,637; 6,085,740; 6,467,476; 6,640,804; 7,174,888; 6,014,970; 6,205,999; 6,755,189; 6,427,682; 6,814,071; 7,066,398; 6,978,941; 7,100,600; 7,032,590; 7,195,011, incorporated herein by reference. These references describe exemplary aerosol generators, ways to manufacture such aerosol generators and ways to supply liquid to aerosol generators, and are incorporated by reference for at least these features. The aerosol generators may comprise vibratable membranes having tapered aperture with a size in the range from about 3 µm to about 8 µm, preferably from about 3 µm to about 6 µm, and in some cases around 4 µm. The membrane may be domed shaped and be vibrated by an annular piezoelectric element that circumscribes the apertures. The diameter of the membrane may be in the range from about 5 mm to about 8 mm. The membrane may also have a thickness in the range from about 50 microns to about 70 microns. Typically, the membrane will be vibrated at a frequency in the range from about 50 kHz to about 150 kHz.

Each time the dispensing system is operated it delivers a metered quantity of the liquid from the unit dose blister 201 to the rear face 109 of the aerosol generator. Hence, for each use a metered quantity of aerosolized pharmaceutical agent is dispensed at the mouthpiece outlet 105 by operation of the aerosol generator.

The blister 201 contains a predetermined volume of an active pharmaceutical agent to be dispensed. In one embodiment the blister 201 contains about 80 to about 120 microliters of insulin. The lower limit is typically at least about 15 micro-liters and the upper limit is typically about 1,000 micro-liters to about 2,000 micro-liters. One particularly useful range is about 80 micro-liters to about 120 micro-liters in a concentration of about 100 insulin units/ml or greater, and more preferably between about 200-800 units/ml, and in some cases as high as 2,500 units/ml. Blister 201 is made of thin-walled deformable material. Due to sensitivity of insulin to mechanical agitation, the blister 201 is filled-up to nearly its entire volume. Specifically, more than 80% of the volume is filled with insulin.

Inhaler 100 further includes a dispensing station configured to dispense the content of the blister 201 to the aerosol generator 108. The dispensing station includes a swivel arm member 104 and a blister seat 107. The blister seat 107 has a concave shape which may radially match the convex shape of the blister 201. The blister seat 107 further includes a hypodermic needle 112 which establishes a fluid passage from the blister to the vibrating aerosol generator 108. The needle 112 has two sections. The first section 112A extends from the dispensing seat and protrudes outwardly perpendicularly to blister seat 107. The second end 112B extends inwardly toward the aerosol generator 108 and is positioned in closed proximity to rear side of the vibrating membrane of aerosol generator 108. Typically, second end 112B will be less than 5 mm and more preferably less than 2 mm from the vibrating membrane of the aerosol generator 108. The hypodermic needle 112 may be made of stainless steel alloy type 316 with a gage size ranging from 22 gage to 26 gage. The first section 112A has a sharp slanted piercing tip. In use, blister 201 is placed upon the concave seat 107 and then the swivel arm 104 is rotated counter clockwise in the direction of arrow 115.

Conveniently, the force upon the swivel arm 104 may be applied by a thumb against the curved portion of the arm 104. This action forces the blister toward the piercing tip of the needle 112A which subsequently pierces the blister 201 and squeezes its content via the needle 112 through the outlet of the needle 112B and onto the aerosol generator 108. When the swivel arm 104 is fully depressed, the entire dose is delivered to the vibrating membrane of the aerosol generator 108.

Figure 2:
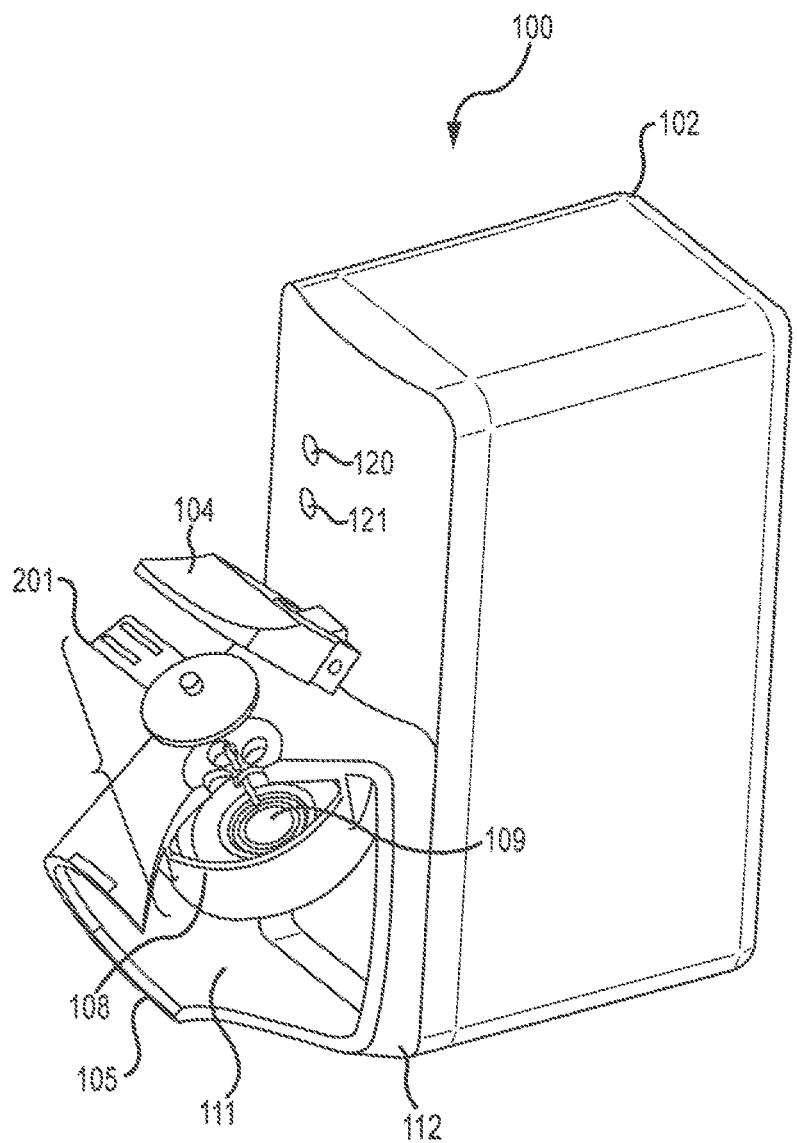

FIG. 2 illustrates the vibrating membrane 109 of the aerosol generator 108 in greater detail. When the content of the blister 201 is fully dispensed an indicator light 120 starts to blink signaling to the patient that the inhaler 100 is ready for use. At any time shortly thereafter the patient may inhale through the mouthpiece 105. Patient inhalation is detected by a flow sensor which in turn activates the aerosol generator 108 to produce aerosol particles into the duct 111. Aerosol is entrained in the inhalation air flow in the direction shown by arrows 121 and flow via the respiratory system to the lungs of the patient. When the entire dose is aerosolized, which may take one or morel breaths, the "end-of-dose" indicator light 121 lights a second time to signal the patient that the entire dose has been delivered. Delivery of the entire dose is obtained when at least about 95% of the dose is delivered, more preferably 98% and most preferably when more than 99% of the dose is delivered. In one embodiment, the opening funnel to the aerosol generator is sufficiently large such that the liquid delivery to the aerosol generator is delivered in its entirety. To receive the dose, the patient may take several inhalations or a single inhalation depending on the volume delivered to the mesh and the patient's breathing capacity. Each inhalation should be a deep breath to assure that the aerosol reaches deeply to the lungs.

When the end-of-dose indicator light 120 is actuated following inhalation of the contents of blister 201, the empty blister may be removed and discarded. When the thumb pressure on the swivel arm 104 is release the blister expands to its original shape. Expansion creates a vacuum inside the blister 201 which draws back any adhered fluid from the needle back to the blister, thereby leaving the interior of the needle dry to prevent material dry-out and clogging. To further prevent possible bacterial contamination the internal and/or the external surfaces of the needle, needle 112 may be coated with silver, a silver based coating or the like.

Figure 3:
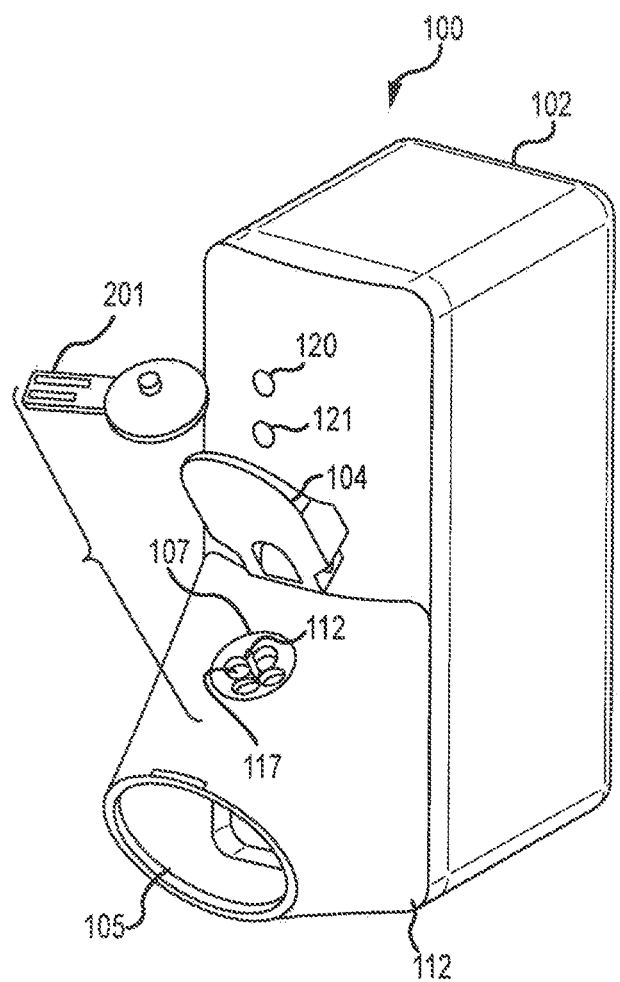

FIG. 3 illustrates the concave seat 107 of the dispensing station in greater detail. Seat 107 is provided with holes 117 which provides access to the interior of the inhaler in the vicinity of the aerosol generator 108. This permits cleaning solvents and rinsing water to be supplied to the aerosol generator 108.

Figure 4:
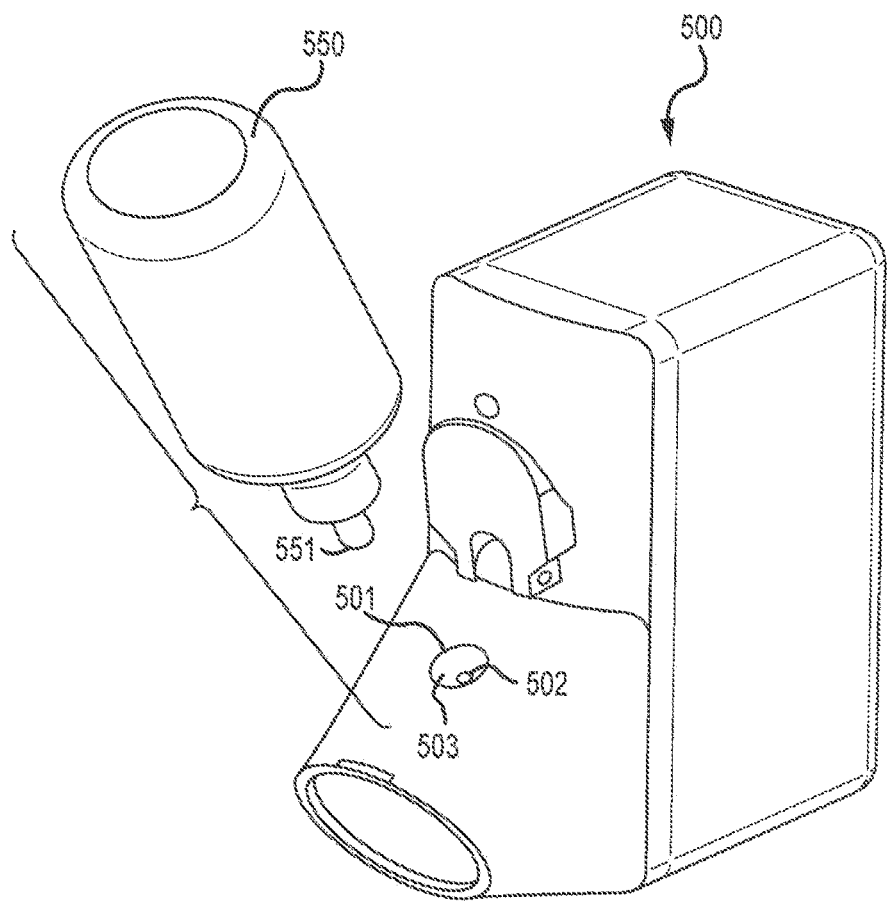

FIG. 4 provides an alternative delivery system for an inhaler 500 which utilizes a preservative free dispenser 550 and a nozzle 551 to dispense a volume of a preservative free pharmaceutical agent to the aerosol generator via an opening 501. Inhaler 500 can be constructed in a manner similar to inhaler 100 and may include a similar aerosol generator. Opening 501 has a funnel shape which tapers down to a small opening 502, thus forming a slope 503. Dispenser 550 is a uniform drop, preservative free dispenser which upon activation displaces a single drop through the tip of its nozzle 551. Preferably, the drop volume is smaller than about 200 micro-liters. A dose is dispensed by squeezing container 550 in a direction perpendicular to its longitudinal axis. Upon each actuation, a single drop of a fixed volume is displaced through the nozzle 551.

Figure 4A:
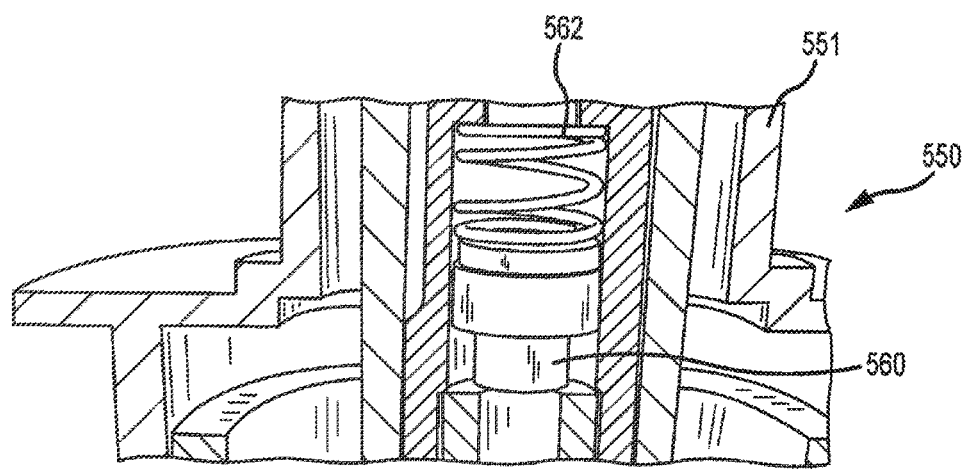
Figure 4B:
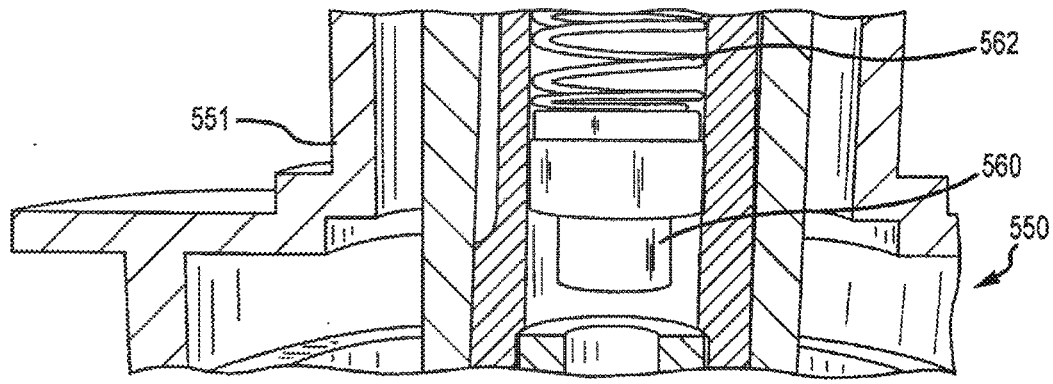

One exemplary dispenser is the Aptar OSD dispenser, developed by Ing. Erich Pfeiffer GmbH. Such a container is constructed of a squeeze bottle that is squeeze to dispense a droplet. When released, the nozzle prevents microbiological contaminants from entering into the remaining liquid. This is accomplished through a tip seal (see, for example, tip seal 560 of FIGS. 4A and 4B) that prevents back flow of liquid into the container. As shown in FIG. 4A, the tip sealing mechanism includes a spring 562 that keeps the tip seal 560 in place in a normally closed position. When squeezing the bottle, liquid passes between the seal 560 and a cap until sufficient pressure is created to overcome the force of the spring 562 (see FIG. 4B). In this way, a single droplet can be dispensed. After dispensing, the tip seal again closes to prevent liquids from moving back into the container. To relieve the accumulating vacuum within the bottle, a small hole is included in the side of the container to allow air into the spring chamber. Droplet size can be controlled based on several factors including top size and the viscosity of the liquid.

In use, nozzle 551 is aligned with the opening 501 such that the drop is dispensed to the slope 503 and flows through the opening 502 to the aerosol generator. Preferably, the angle of slope 503 is greater than about 30 degrees relative to the axis of the opening 502. The diameter of opening 501 is about 10 mm to about 15 mm and the diameter of opening 502 is at least about 5 mm. The pharmaceutical fluid in the preservative free dispenser 550 may be contained in a collapsible sack to prevent excessive agitation and which may damaged by mechanical sloshing. For example, proteins, such as insulin, may be sensitive to mechanical agitation. Use of a collapsible sack may limit undesirable agitation.

Figure 5:
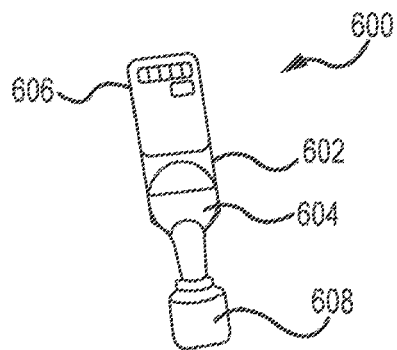

In another alternative embodiment, instead of using a container of the type described in FIG. 5, a container 600 could be used. Container 600 comprises a blister 602 manufactured using a blow-fill-seal process. Container 600 is similar to the container 201 of FIG. 1 in that when the blister 602 is squeezed a unit dosage amount is delivered.

Blister 602 comprises a squeezable body 604 having a tab 606 and a twist off top 608. Body 604 is sized to hold a unit dosage of liquid, and tab 66 may include various types of identifying information, such as the lot number, date, and the like. Twist off top 608 provides a easy way to open blister 602 so that the liquid can be dispensed.

Figure 6:
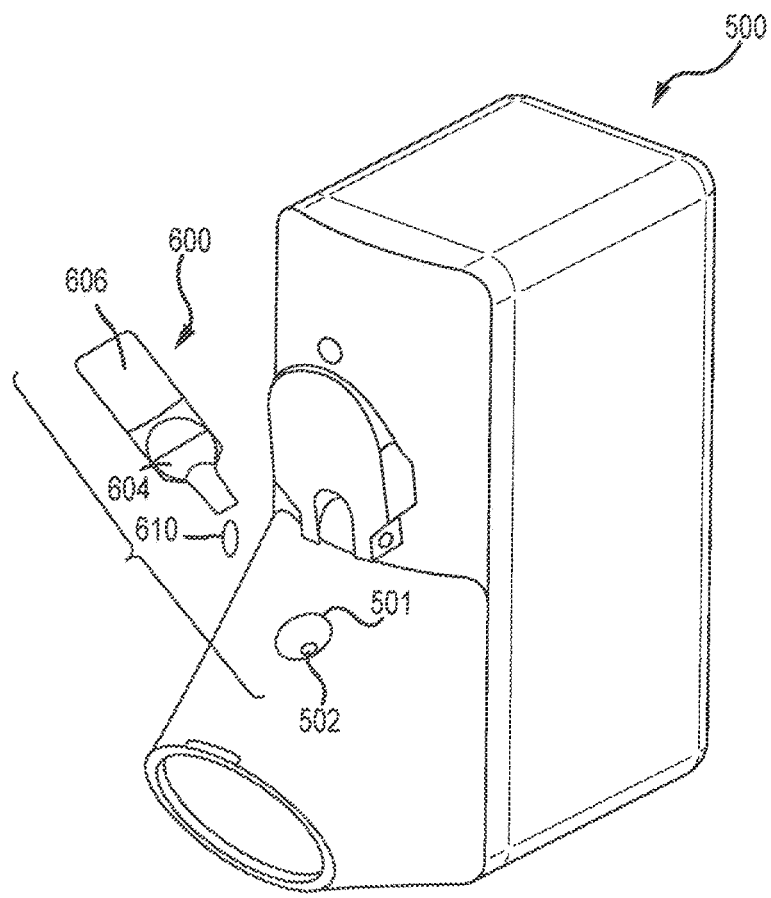
FIG. 6 illustrates the container of FIG. 5 when dispensing a unit volume of liquid into the dispensing apparatus of FIG. 4.

Referring also to FIG. 6, use of blister 602 in supplying a unit dose of liquid to inhaler 500 will be described. When ready to receive a treatment, a user takes blister 602 and twists off top 608. Typically, blister 602 will be held upright so that no liquid escapes. In some cases, the opening formed when top 608 is removed may be sized small enough to hinder liquid from escaping. Blister 602 is moved over opening 501 and body 604 is squeezed to expel the complete volume of liquid 610 into opening 501 where the liquid drains through opening 503 and to the aerosolizer. In this way, blister 602 functions as a hand squeezable, single use container for a preservative free solution. Use of a blow-fill-seal process is particularly advantageous in that the blister 602 can be manufactured at low cost while still allowing the storage of a preservative free solution. Also, the metering process is simple, requiring only the removal of the top and squeezing of the blister.

Figure 7:
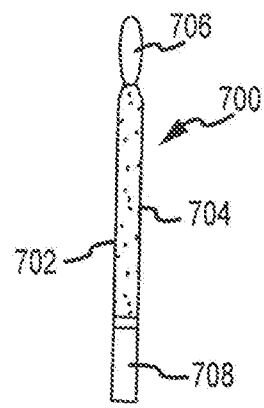
FIG. 7 illustrates an embodiment of an ampoule for dispensing a unit volume of a liquid according to the invention.

FIG. 7 illustrates an embodiment of an ampoule 700 for dispensing a unit volume of a liquid to be aerosolized. Ampoule 700 comprises an elongate body 702 defining a capillary that hold a unit volume of liquid 704. Ampoule 700 further includes a top end 706 and a bottom end 708 that may be removed from body 702, such as by snapping them off. Body 702 may be constructed of a generally rigid material that has sufficient rigidity to permit the two ends to be easily snapped off.

Figure 8:
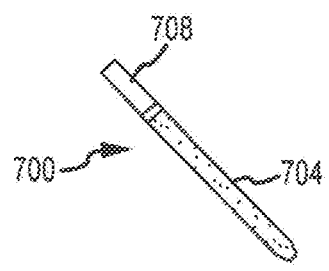
FIG. 8 illustrates the ampoule of FIG. 7 with an end removed.

When ready to dispense the liquid into an inhaler, top end 706 is removed as illustrated in FIG. 8. The surface tension in body 702 prevents leakage of any liquid 704 when ampoule 700 is inverted, such as when inserting ampoule 700 into an inhaler.

Figure 9:
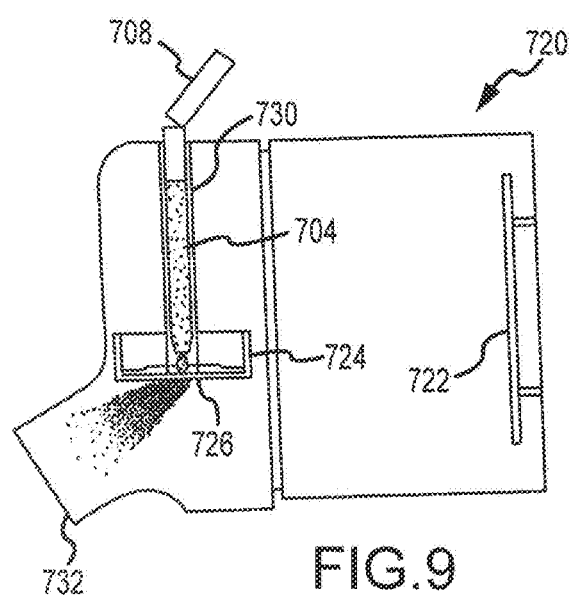
FIG. 9 illustrates the ampoule of FIG. 8 with the top end also removed and being deposited into a dispensing apparatus.

FIG. 9 illustrates the ampoule of FIG. 8 after being inserted into an inhaler 720. Inhaler 720 may be constructed in a manner similar to the other embodiments described herein an includes electronics 722 that are employed to control operation of an aerosol generator 724 having a vibratable mesh 726. Inhaler 720 includes an elongate opening 730 into which ampoule 700 is inserted after end 706 is removed. Once in place, end 708 is snapped off which allows liquid 704 to drain from ampoule 700 and onto the rear face of vibratable mesh 726 as illustrated in FIG. 9. As mesh 726 vibrates, the liquid is aerosolized and directed toward a mouthpiece 732 where the patient can inhale the medicament. Following aerosolization, ampoule 700 may be removed from inhaler 720 and discarded.

Figure 10:
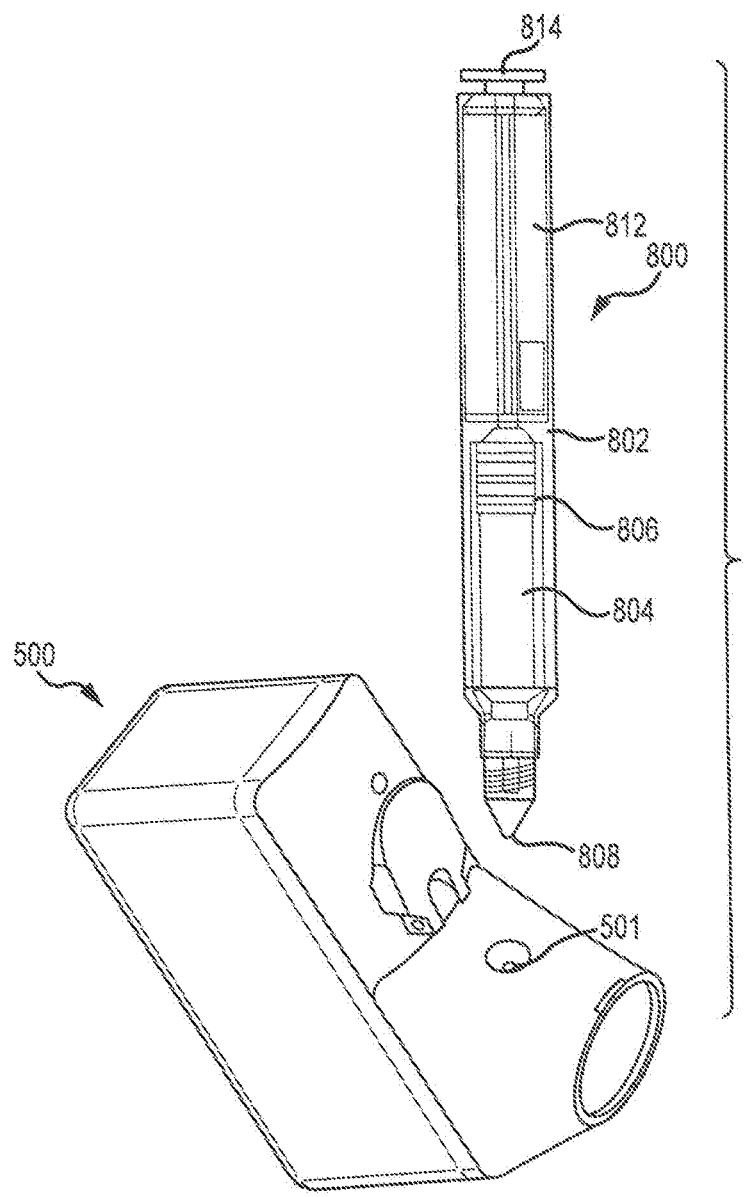
FIG. 10 illustrates another embodiment of a container for dispensing a unit volume of a liquid into the dispensing apparatus of FIG. 4.

FIG. 10 illustrates another embodiment of a container 800 for dispensing a unit volume of a liquid into the dispensing apparatus 500 that was previously described in connection with FIG. 4. Container 800 comprises a container body 802 defining a reservoir 804 for holding a volume of liquid to be dispensed. A plunger 806 is employed to force liquid in reservoir 804 through a dispensing end 808 of container 800. Container 800 also includes a geared metering mechanism 812 that is rotated or "dialed" in order to control the extent of movement of plunger 806. Further, an actuator 814 is pressed to move the plunger 806 by the amount permitted by metering mechanism 812. In this way, a user can simply "dial a dose" of liquid using metering mechanism 812 and then press actuator 814 in order to dispense a metered amount of liquid into hole 501 where it will be supplied to the aerosolization mechanism.

Container 800 can be configured to be disposable or reusable. When reusable, reservoir 804 may comprise a cartridge that is inserted into the space defined by reservoir 804. Exemplary volume sizes may be about 1, 1.8 or 3 ml cartridges, which may be constructed of glass, LDPE or the like.

The invention has now been described in detail for purposes of clarity and understanding. However, it will be appreciated that certain changes and modifications may be practiced within the scope of the appended claims.

What is claimed is:

1. A method of aerosolizing a volume of liquid medicament, comprising:
   providing an inhaler, comprising:
      a housing comprising a mouthpiece and a liquid receptacle fluidly coupled to the mouthpiece, wherein the liquid receptacle defines an opening that extends through an exterior surface of the housing at an inlet end of the opening;
      an aerosol generator disposed within the housing, the aerosol generator comprising:
         a membrane having a front face, a rear face, and a plurality of apertures that extend between the front face and the rear face; and
         a vibratable element; and
      a visual indicator, wherein an inlet end of the opening is positioned between, and in general alignment with, the mouthpiece and the visual indicator, with the visual indicator and the opening being positioned on a same surface of the housing and the visual indicator being oriented such that the visual indicator is visible to a user of the inhaler while the user inhales through the mouthpiece;
   detecting fluid flow through the mouthpiece as the user inhales using a flow sensor;
   activating the vibratable element in response to detecting the fluid flow to aerosolize a dosage of the liquid medicament that has been supplied to the rear face of the membrane as the user inhales via the mouthpiece; and
   providing, using the visual indicator, an indication that the entire dosage of liquid has been aerosolized.

2. The method of aerosolizing a volume of liquid medicament of claim 1, further comprising:
   providing, using the visual indicator, an indication that the dosage of liquid medicament has been received within a receiving chamber within the housing.

3. The method of aerosolizing a volume of liquid medicament of claim 2, wherein:
   the visual indicator comprises a first light that provides the indication that the dosage of liquid medicament has been received within the receiving chamber and a second light that provides the indication that the entire dosage of liquid has been aerosolized.

4. The method of aerosolizing a volume of liquid medicament of claim 3, wherein:
providing the indication that the dosage of liquid medicament has been received within the receiving chamber comprises blinking the first light.

5. The method of aerosolizing a volume of liquid medicament of claim 1, wherein:
the housing comprises a funnel coupled with the opening, the funnel directing the liquid medicament to the rear face of the membrane.

6. The method of aerosolizing a volume of liquid medicament of claim 5, wherein:
a slope of the funnel is at least 30 degrees relative to a central axis of the opening.

7. A method of aerosolizing a volume of liquid medicament, comprising:
providing an indication that a dosage of the liquid medicament has been received by an inhaler via an opening formed through a housing of the inhaler;
detecting fluid flow through a mouthpiece of the inhaler as a user inhales through the mouthpiece using a flow sensor of the inhaler;
activating an aerosol generator of the inhaler in response to detecting the fluid flow to aerosolize the dosage of liquid medicament that has been supplied to a rear face of a membrane of the aerosol generator as the user inhales via the mouthpiece; and
providing an indication that the entire dosage of liquid has been aerosolized using a visual indictor of the inhaler, wherein an inlet end of the opening is positioned between, and in general alignment with, the mouthpiece and the visual indicator, with the visual indicator and the opening being positioned on a same surface of the housing and the visual indicator being oriented such that the visual indicator is visible to the user while the user inhales through the mouthpiece.

8. The method of aerosolizing a volume of liquid medicament of claim 7, wherein:
the visual indicator is positioned in alignment with a center of the mouthpiece along a central axis of the inhaler.

9. The method of aerosolizing a volume of liquid medicament of claim 7, wherein:
the inhaler comprises a funnel that directs the dosage of liquid medicament to the rear face of the membrane.

10. The method of aerosolizing a volume of liquid medicament of claim 9, wherein:
the funnel comprises a maximum diameter of between about 10 mm and 15 mm and an opening to the funnel is at least 5 mm.

11. The method of aerosolizing a volume of liquid medicament of claim 7, wherein:
the aerosol generator comprises a vibratable element that vibrates the membrane.

12. The method of aerosolizing a volume of liquid medicament of claim 11, wherein:
the vibratable element vibrates at a rate of between about 50 kHz to 150 kHz.

13. The method of aerosolizing a volume of liquid medicament of claim 7, wherein:
delivery of the entire dosage comprises delivery of 98% or more of the liquid medicament received by the inhaler.

14. A method of aerosolizing a volume of liquid medicament, comprising:
detecting fluid flow through a mouthpiece of an inhaler as a user inhales through the mouthpiece using a flow sensor of the inhaler;
activating an aerosol generator of the inhaler in response to detecting the fluid flow to aerosolize a dosage of the liquid medicament that has been supplied to the aerosol generator via an opening formed through a housing of the inhaler as the user inhales via the mouthpiece; and
providing an indication that the entire dosage of liquid has been aerosolized using a visual indictor of the inhaler, wherein an inlet end of the opening is positioned between, and in general alignment with, the mouthpiece and the visual indicator, with the visual indicator and the opening being positioned on a same surface of the housing and the visual indicator being oriented such that the visual indicator is visible to the user while the user inhales through the mouthpiece.

15. The method of aerosolizing a volume of liquid medicament of claim 14, wherein:
activating the aerosol generator comprises vibrating a vibratable member that is coupled with a dome-shaped membrane.

16. The method of aerosolizing a volume of liquid medicament of claim 14, wherein:
the visual indicator comprises at least one light.

17. The method of aerosolizing a volume of liquid medicament of claim 14, wherein:
an exterior housing of the inhaler defines the opening through which the liquid medicament is delivered to the aerosol generator; and
the opening and the visual indicator are disposed on a same wall of the exterior housing.

18. The method of aerosolizing a volume of liquid medicament of claim 14, further comprising:
providing an indication that the dosage of liquid medicament has been received by the inhaler.

* * * * *